(12) United States Patent
Matusch

(10) Patent No.: US 8,973,621 B2
(45) Date of Patent: Mar. 10, 2015

(54) METHOD AND DEVICE FOR FILLING A DISPOSABLE INJECTOR

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 1040 days.

(21) Appl. No.: 12/932,772

(22) Filed: Mar. 5, 2011

(65) Prior Publication Data

US 2011/0214777 A1 Sep. 8, 2011

(30) Foreign Application Priority Data

Mar. 8, 2010 (DE) .......................... 10 2010 010 699

(51) Int. Cl.
| | |
|---|---|
| B65B 1/04 | (2006.01) |
| B65B 3/00 | (2006.01) |
| A61M 5/178 | (2006.01) |
| A61M 5/20 | (2006.01) |
| A61M 5/31 | (2006.01) |

(52) U.S. Cl.
CPC .............. *B65B 3/003* (2013.01); *A61M 5/1782* (2013.01); *A61M 5/2033* (2013.01); *A61M 2005/3121* (2013.01)
USPC .................... 141/2; 141/18; 141/23; 141/329

(58) Field of Classification Search
CPC ............................ B65B 3/003; A61M 5/1785
USPC ....................... 141/2, 18, 21, 23, 27, 329, 330
See application file for complete search history.

(56) References Cited

U.S. PATENT DOCUMENTS

| | | | | |
|---|---|---|---|---|
| 3,330,282 | A | * | 7/1967 | Visser et al. .................... 604/90 |
| 3,610,297 | A | | 10/1971 | Raaf et al. |
| 6,755,220 | B2 | * | 6/2004 | Castellano et al. ............. 141/27 |
| 6,773,427 | B2 | * | 8/2004 | Takagi .......................... 604/415 |
| 6,779,566 | B2 | * | 8/2004 | Engel ............................. 141/25 |
| 7,059,368 | B2 | * | 6/2006 | Filler ............................ 141/329 |
| 7,757,724 | B2 | * | 7/2010 | Li et al. .......................... 141/59 |
| 8,122,922 | B2 | * | 2/2012 | Baker ........................... 141/326 |
| 8,720,501 | B2 | * | 5/2014 | Thilly .......................... 141/329 |
| 2003/0139707 | A1 | | 7/2003 | Hommann |
| 2004/0134562 | A1 | * | 7/2004 | Engel ............................ 141/329 |
| 2007/0265575 | A1 | | 11/2007 | Hillios et al. |
| 2010/0106090 | A1 | | 4/2010 | Matusch |

\* cited by examiner

*Primary Examiner* — Jason K Niesz
(74) *Attorney, Agent, or Firm* — R.S. Lombard; K. Bach

(57) ABSTRACT

The invention relates to a method and a device for the sterile filling of a disposable injector with a defined dose of an injection solution, wherein the disposable injector comprises a cylinder/piston unit with a cylinder and with a piston that can be pulled back manually. The defined dose of the injection solution is stored in an interior of a container of a needle syringe held in a bored stopper. The cylinder interior is connected to the container interior in a gas-tight and liquid-tight manner through the bored stopper. The cylinder/piston unit is filled by pulling back the piston or by pressing the needle syringe piston. With the present invention, a method and a device for filling a disposable injector are developed in which, without intermediate weighing or risk of inaccurate readings, the disposable injector can be filled with a defined dose of an injection solution from a syringe with a fused-in needle.

10 Claims, 3 Drawing Sheets

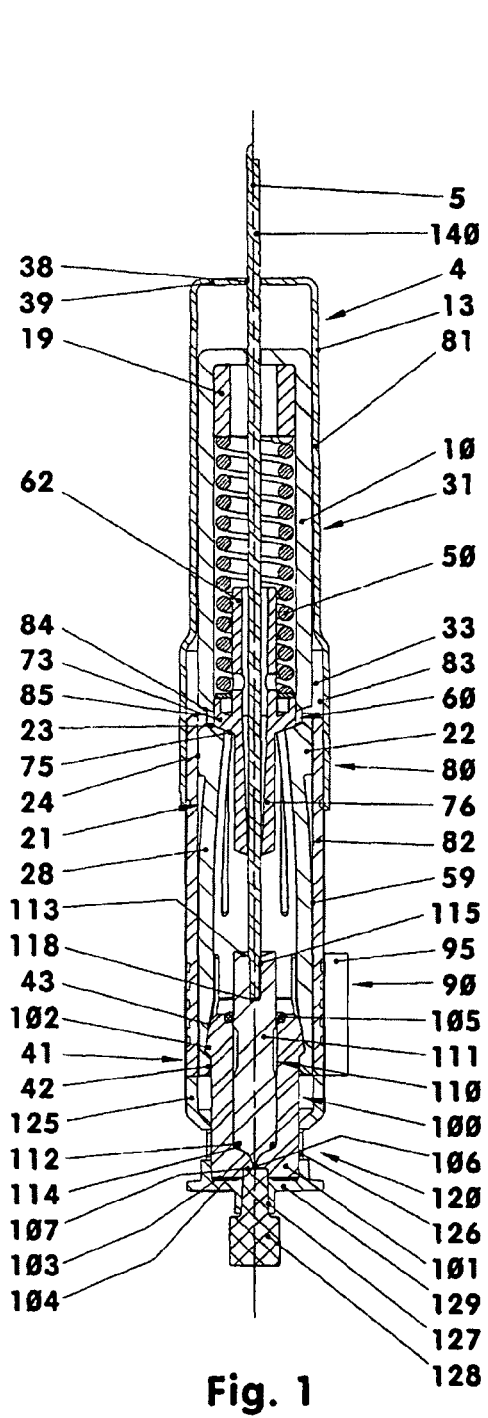
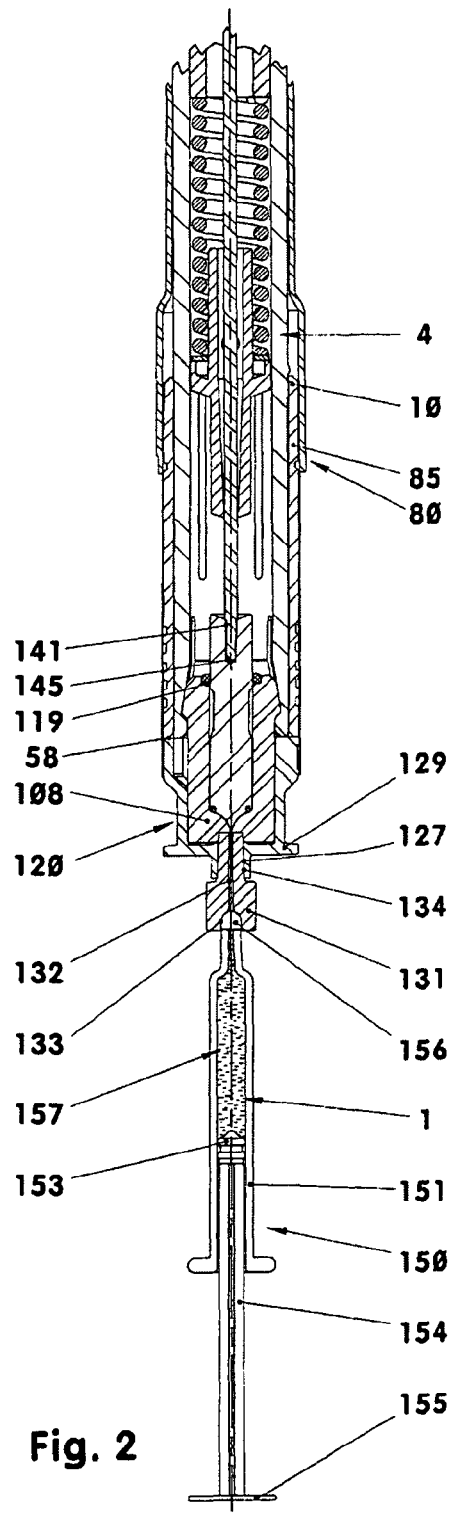
Fig. 1
Fig. 2

US 8,973,621 B2

METHOD AND DEVICE FOR FILLING A DISPOSABLE INJECTOR

CROSS-REFERENCE TO RELATED APPLICATION

This application claims the priority of German Application No. DE 10 2010 010 699.2 filed Mar. 8, 2010.

BACKGROUND OF THE INVENTION

The invention relates to a method and a device for the sterile filling of a disposable injector with a defined dose of an injection solution, wherein the disposable injector comprises a cylinder/piston unit with a cylinder and with a movable piston that can be operated manually by means of a rod.

Self-fill single-chamber systems can only be filled using syringes without a needle. However, if an injection solution is stored in a syringe with a fused-in needle, the content first has to be introduced into a syringe without a needle and weighed, which is problematic in the case of batches for clinical trials on account of the additional possible sources of error.

DE 10 2007 034 871 A1 discloses a disposable injector in which the injection solution is sucked out of a medicament ampule through a hose adapter. The dosing is carried out using a scale on a pump rod with which the piston of a cylinder/piston unit is actuated. The dosed amount can vary depending on the angle at which the scale is viewed.

The problem addressed by the present invention is therefore that of developing a method and a device for the sterile filling of a disposable injector in which, without intermediate weighing or risk of inaccurate readings, the disposable injector can be filled with a defined dose of an injection solution, even when the dose is located in a syringe with a fused-in needle.

SUMMARY OF THE INVENTION

The invention relates to a method and a device for the sterile filling of a disposable injector with a defined dose of an injection solution, wherein the disposable injector comprises a cylinder/piston unit with a cylinder and with a piston that can be pulled back manually. The defined dose of the injection solution is stored in an interior of a container of a needle syringe held in a bored stopper. The cylinder interior is connected to the container interior in a gas-tight and liquid-tight manner through the bored stopper. The cylinder/piston unit is filled by pulling back the piston or by pressing the needle syringe piston.

With the present invention, a method and a device for filling a disposable injector are developed in which, without intermediate weighing or risk of inaccurate readings, the disposable injector can be filled with a defined dose of an injection solution from a syringe with a fused-in needle.

The cylinder interior is connected to the container interior in a gas-tight and liquid-tight manner through the bored stopper.

The cylinder/piston unit is filled by pulling back the piston thereof or by pressing the needle syringe piston.

BRIEF DESCRIPTION OF THE DRAWINGS

Further details of the invention will become clear from the following schematically depicted illustrative embodiments, in which:

FIG. 1 shows a disposable injector before filling;
FIG. 2 shows FIG. 1 with a needle syringe attached.

DETAILED DESCRIPTION OF THE PARTICULAR EMBODIMENTS

Figure 3:
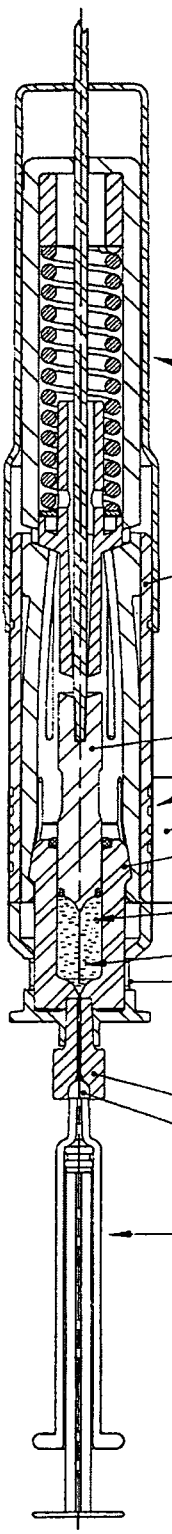
FIG. 3 shows a filled disposable injector.

FIG. 1 shows a disposable injector (4). Injectors of this kind can be used just once. After use, they are locked against being used again.

The disposable injector (4) comprises a housing (10), a spring-energy reservoir (50), a piston-actuating ram (60), a trigger unit (80), a cylinder/piston unit (100) and a tamper-evident seal (90).

The housing (10) is a pot-shaped hollow body open at the bottom, and with a floor (39) lying at the top. It is produced, for example from a glass-fiber-reinforced polyamide, by injection molding. The housing (10) has a substantially tubular configuration and is divided into two functional areas, which are, on the one hand, the upper jacket area (31) and, on the other hand, the lower fixing area (41). In the jacket area (31), the housing (10) has, for example, two window-like apertures (33) lying opposite each other. A pressure rod (21) is in each case mounted in an articulated manner on the lower edge of the individual aperture (33). The floor (39) has a central bore (38).

The pressure rod (21) has, for example along 80% of its length, the wall thickness and the curvature of the wall of the housing (10). This area also has the function, among others, of a resilient flexural beam (28). It has a sickle-shaped cross section.

If appropriate, a part of this flexural beam (28) can also be provided with a rectangular cross section in order to reduce bending stresses that occur in the edge area of the flexural beam during use.

The upper free end of the individual pressure rod (21) is here formed by the radially outwardly protruding cam (22). The latter has at least one support surface (23) oriented in the direction of the center line (5), and a contact surface (24) directed away from the center line (5).

The lower half of the housing (10) is surrounded by the sleeve-shaped trigger element (82). The latter is, for example, substantially cylindrical, and it is made of acrylonitrile-butadiene-styrene (ABS) copolymer, for example. The trigger element (82) is mounted so as to be movable along the radial outer surface (13) of the housing (10). It ends at the rear with a sharp edge (85), which is part of a return flank (84) at the end face of the trigger element (82). Below the edge (85), according to FIG. 1, the cams (22) formed integrally on the pressure rods (21) securely touch the inside wall (59) of the trigger element (82) with their outer contact surfaces (24).

Figure 8:
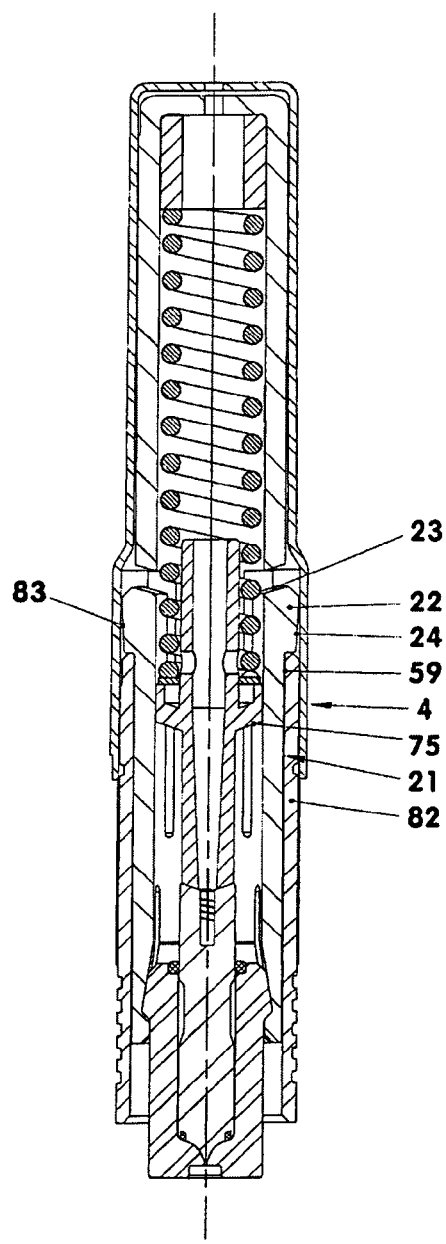

A trigger cap (81) completely surrounding the rear end of the housing (10) is secured on the trigger element (82), for example near the edge (85). The trigger cap (81) comprises a circumferential widened area (83), in which the cams (22) are received when the injector is triggered (cf. FIG. 8). Instead of this widened area (83), partial widened areas or uncovered openings can also be provided per pressure rod (21) in the case of a non-rotationally symmetrical trigger element (82). Above the widened area (83), the trigger cap (81) bears slidably on the outer wall (13) of the housing (10).

The piston-actuating ram (60) arranged in the housing (10) is divided into two areas. The lower area is the piston slide (76). The diameter thereof is slightly smaller than the internal diameter of the rear area of the cylinder (101) of a cylinder/piston unit (100). The lower end face of the piston slide (76) acts directly on the piston (111) of this cylinder/piston unit (100).

The upper area of the piston-actuating ram (60), i.e. the ram plate (73), is a flat, at last partially cylindrical disk, of which the external diameter is several tenths of a millimeter smaller than the internal diameter of the housing (10) in the jacket area (31). The lower end face has a collar surface (75) arranged around the piston slide (76). It has the shape of a truncated cone jacket, of which the vertex angle is ca. 100 to 140 degrees. In the illustrative embodiment shown, the collar surface (75) has a vertex angle of 140 degrees. The imaginary vertex of the truncated cone jacket lies on the center line (5) in the area of the piston slide (76). The collar surface (75) can also have a spherical curvature.

The piston slide (76) can of course also be designed as a component separate from the ram plate (73). To this end, it is then guided on the inside wall of the housing (10).

The helical compression spring (50) sits pretensioned between the ram plate (73) and the floor (39) lying at the top of the housing (10). The helical compression spring (50) bears on the floor (39) of the housing (10), for example via a spacer sleeve (19). The spring force of the helical compression spring (50) is transferred to the pressure rods (21) via the ram plate (73). On account of the inclination of the collar surface (75), the pressure rods (21) are forced radially outward in the manner of a spline gear. The trigger sleeve (82) permanently supports this radial force.

Above the ram plate (73), the piston-actuating ram (60) has a guide pin (62). The latter guides the helical compression spring (50) or is guided by the latter. Below the ram plate (73), the piston slide (76) is located centrally in the continuation of the guide pin (62).

The fixing area (41) for receiving the insertable cylinder/piston unit (100) is located below the jacket section (31). The fixing area (41) comprises, for example, eight spring hooks (42) oriented parallel to the center line (5). The spring hooks (42) each have an at least two-flanked undercut (43) for receiving the cylinder/piston unit (100) free of play. The mutually opposite flanks of the undercut (43) enclose an angle of 90 degrees, for example. The length and the spring rate of the spring hooks (42) are dimensioned such that the cylinder/piston unit (100) can be inserted without plastic deformation of the spring hooks (42).

The cylinder (101), which in the illustrative embodiment, as shown in FIG. 1, can be filled with water for injection or with an injection solution (1), is, for example, a transparent, thick-walled pot, of which the optionally cylindrical outer wall supports, for example, a circumferential locking ring (102) that bears in a dimensionally stable manner on the flanks of the undercut (43) of the spring hooks (42). The rodless piston (111) sits in the for example cylindrical or conical bore of the cylinder (101). At its front and at least approximately conical end face, the piston (111), produced for example from the Teflon (a U.S. registered trademark of E. I. Dupont De NeMours and Company of Wilmington, Del. 19898) derivative tetrafluoroethylene/hexafluoropropylene copolymer (FEP), has an axial annular groove (112) for receiving a sealing ring (114) or a permanently elastic sealing compound. If appropriate, a for example cylindrical metal plate is let into the rear end face of the piston (111). In the view in FIG. 1, the piston (111) is sitting in the forward position. Its upper end protrudes from the cylinder (101). The length of the piston (111) is chosen such that the inserted piston (111), cf. FIGS. 1 and 8, protrudes by at least one millimeter above the rear upper edge. The central area of the piston (111) is narrowed. The circumferentially narrowed area has a length corresponding to ca. 30% of the overall length of the piston. The narrowed area has a diameter that is 16 to 20% smaller than the maximum internal diameter of the cylinder in the area of the cylinder interior (110) receiving the solution. The front transition, which lies between the narrowed area and the front piston area, i.e. in this case the piston area lying at the bottom, has a cone angle of, for example, 35 to 40 degrees. The other transition, i.e. the rear transition, has a cone angle of between 35 and 90 degrees.

In, the rear, for example frustoconical, end face (113) of the piston (111), there is a central, conical piston recess (115) with the floor (118) for coupling the pump rod (140). The cone angle of the piston recess (115) is, for example, one degree. At its lower end, the pump rod (140) has, for example, a conical V-thread (141) for coupling to the piston (111). The cone angle of the V-thread (141) is six degrees, for example. When the pump rod (140) is turned into the piston recess (115), the thread pitch of the V-thread (141) presses in the necessary counter-thread. The turning-in operation is completed when the front end of the pump rod (140) contacts the floor (118) via the narrow tip of the frustoconical end face (145).

A short cylindrical, nozzle-like bore (106) is located in the center of the bore of the cylinder (101), of which the cylinder floor is at least partially adapted to the contour of the front end face of the piston. The bore (106) has a diameter of ca. 0.1 to 0.5 millimeter. This bore (106) is one to five times as long as its diameter. It ends in a cylindrical recess (107) of the outer end face (103) of the floor of the cylinder (101). This end face (103) can additionally be provided with an adhesive ring (104) in order to increase the safety of use.

The closure cap (120), centered on the cylinder (101) of the cylinder/piston unit (100), bears on the lower end face of the trigger element (82). The at least approximately cylindrical outer surface of the closure cap (120) has the same diameter as the likewise cylindrical outer surface of the trigger element (82) near the end face (58).

The closure cap (120) is a beaker, which surrounds and rests tightly against at least the lower quarter of the cylinder/piston unit (100). A part of the closure cap (120) bears with its pot area (125) on the cylindrical outer wall of the cylinder (101) and on the lower end face (103) with the adhesive ring (104) secured thereon.

The pot area (125) has two windows (126) lying opposite each other. The windows (126) have a width that corresponds at least to the diameter of the piston (111). The lower edge of the windows (126), that is to say the edges lying nearest the plate-like foot (129) are arranged at the height of the cylinder floor (108). With the aid of the windows (126) and the light transmitted through them, it is possible to check, among other things, the freedom of the cylinder content from bubbles. On the plate-like foot (129), a conical tube section, for example, is formed integrally as adapter opening (127). The adapter opening (127) has, as its inner wall, a Luer internal cone at least in sections. According to FIG. 1, the adapter opening (127) is closed in a sterile manner by means of a closure stopper (128). For this purpose, the closure stopper (128) has, for example, a Luer external cone, with which it sits with a force fit in the adapter opening (127) and at the same time also closes the recess (107) of the cylinder (101) in a sterile, gas-tight and liquid-tight manner.

To provide safety prior to triggering, the closure cap (120) is connected to the trigger element (82) of the injector (4) by way of a banderole (90). The banderole (90) is a tamper-evident seal configured as an adhesive label.

The banderole (90) itself is, for example, a strip of paper and/or film coated in some areas of one side with an adhesive. It is composed, for example, of three separate strips, which can be separated from one another in each case via a perforation or via another predetermined breaking point.

Figure 5:
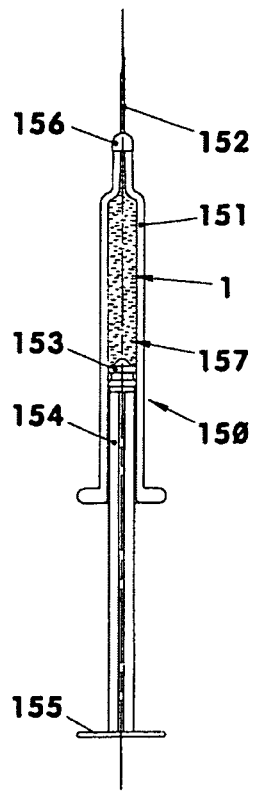
FIG. 5 shows a needle syringe with injection solution.
Figure 6:
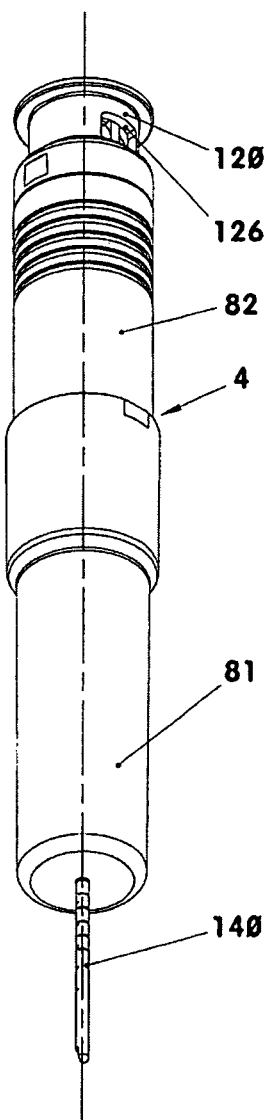
FIG. 6 shows a disposable injector with pump rod.

FIG. 2 shows the disposable injector (4) with a needle syringe (150) attached thereto. In the illustrative embodiment, the needle syringe (150) (cf. FIG. 5) has a glass cylinder (151) with a fused-in needle (152). The needle (152) can be separated from the glass cylinder (151) only by destroying the latter. The head (156) of the glass cylinder (151) oriented in the direction of the needle (152) has a spherical cap shape. A piston (153) with a piston rod (154) and an actuating ram (155) is guided in the glass cylinder (151). The needle syringe (150) is filled, for example, with an individual dose of 0.4 milliliters, for example, of the active-substance-containing injection solution (1) Clexane.

Figure 4:
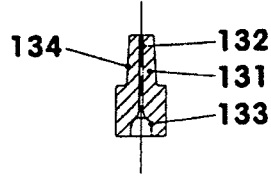
FIG. 4 shows a bored stopper.

The closure stopper (128) shown in FIG. 1 has been replaced in FIG. 2 by a bored stopper (131), of which the bore (132) is at least as long as the needle (152). If appropriate, the bored stopper (131) can have a sterile membrane and serve as a tamper-evident seal for the needle syringe (150). When fitted into the injector (4) for filling, the needle (152) pierces the membrane. For example, the bored stopper (131) adheres to the closure cap (120), for example via an external cone (134), with a force fit and/or form fit and closes the recess (107) of the barrel (101) in a sterile, gas-tight and liquid-tight manner. This double-cone adapter (131), shown as an individual part in FIG. 4, is made, for example, from a synthetic thermoplastic, e.g. polyethyelene. However, it can also be made from stainless steel, glass, titanium, natural rubber, etc. The cross section of the through-bore (132) oriented in the longitudinal direction of the stopper corresponds, for example, to at least the needle cross section. At its end facing away from the nozzle bore (106), this Luer stopper has a recess (133), e.g. an internal cone (133), surrounding the through-bore (132). This recess (133), e.g. of concave shape, receives the head (156) of the needle syringe (150) in a gas-tight and liquid-tight manner, while the through-bore (132) engages around the needle (152) with minimal play. The needle syringe (150) is fixed in the bored stopper (131) in a gas-tight and liquid-tight manner or is locked therein.

To be able to use the disposable injector (4), the cylinder/piston unit (100) has to be filled. For this purpose, all of the injection solution (1) stored in the needle syringe (150) is forced or sucked into the cylinder (101) by pressing in the needle syringe piston (153) by means of the piston rod (154) or by pulling back the piston (111) by means of the pump rod (140). The injection solution (1) flows out of the container interior (157) into the cylinder interior (110), which is connected thereto in a gas-tight and liquid-tight manner. For filling by suction, the pump rod (140) is pulled manually along its entire stroke from the forward to the rearward end position. The rear sealing element (105) remains in position on the collar (119), even when the narrowed area of the piston (111) passes the sealing element (105). Once the piston (111) reaches its rear position, the sealing element (105) again bears radially on the piston (111) and provides a sterile seal. The combination of the sealing elements (114) and (105) also ensures a sterile cylinder interior (110) during the pump movement of the piston (111). FIG. 3 shows the filled disposable injector (4). The suction procedure is completed when the gas bubbles, which may have been sucked into the cylinder (101), are removed in a known manner, e.g. by pushing the piston (111) or the piston (153) back slightly while holding the closure cap (120) at the top. The two windows (126) arranged in the closure cap (120) can be used to check the procedure. The for example graduated pump rod (140) can now be turned out of the recess (115) of the piston (111) and pulled out of the housing (10). The defined individual dose of the medicament (1) is now stored in the cylinder (101) of the cylinder/piston unit (100).

The needle syringe (150) with the bored stopper (131) can now be detached from the closure cap (120) and from the cylinder (101).

After the cylinder (101) has been charged and, if appropriate, any air removed from it, the filled injector can be stored on an interim basis when the nozzle bore (106), together with the recess (107), has been closed off again at the front in a sterile, gas-tight and liquid-tight manner by means of a sterile stopper (128). This stopper (128) also adheres with a force fit and/or form fit in the closure cap (120).

Figure 7:
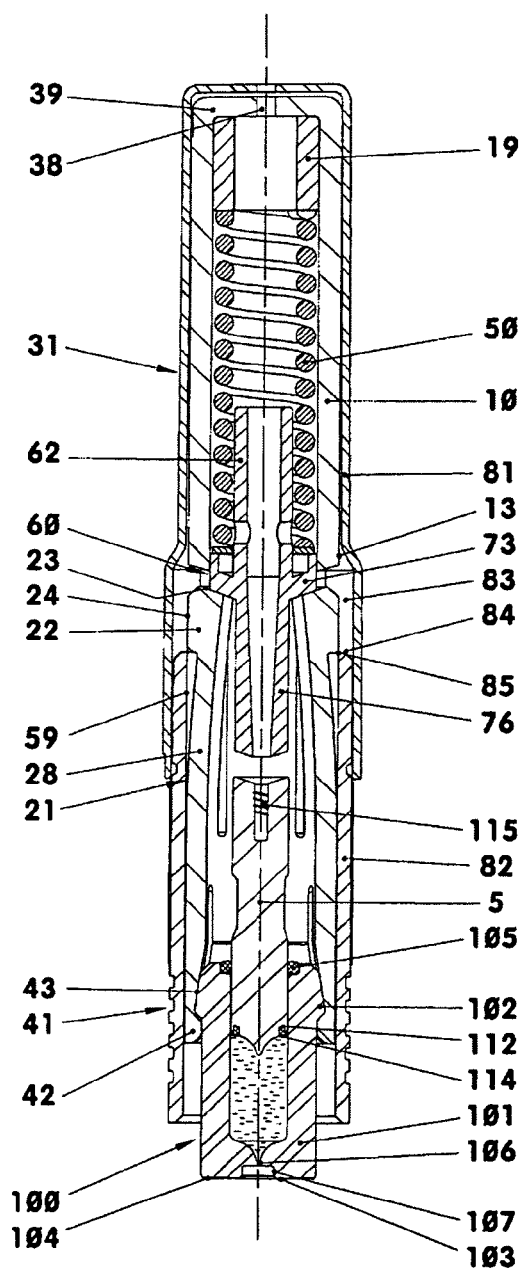
FIG. 7 shows a disposable injector prior to triggering, without pump rod; and,
FIG. 8 shows a disposable stopper after triggering, without pump rod.

To activate the disposable injector, the tear-off banderole (90) is separated all the way round from the main part with the aid of the tear-off tab (95). The closure cap (120) is now pulled downward with the stopper (128) from the cylinder (101) (cf. FIG. 7).

The injector is now placed on the injection site and the sleeve-shaped trigger unit (80) is pushed down in the direction of the injection site. The pressure rods (21) bend elastically outward into their actual starting position. The cams (22) slip outward over the edge (85) into the widened area (83). The now no longer deformed pressure rods (21) free the piston-actuating ram (60), such that the piston (111), under the effect of the spring element (50), moves abruptly downward, with emptying of the cylinder (101) (cf. FIG. 8). During the forward movement of the piston (111), the piston friction temporarily decreases, since the rear sealing element (105) does not bear with a braking action as the narrowed piston area passes it. The injection solution (1) is delivered into the injection site.

LIST OF REFERENCE SIGNS 1 injection solution; medicament
4 disposable injector, injector
5 center line of the injector, longitudinal direction
10 housing, one-piece
13 outer surface, cylindrical
19 spacer sleeve
21 pressure rods, support rods; draw hooks
22 cam
23 support surface
24 contact surface
28 flexural beam
31 jacket area
33 apertures
38 bore
39 floor
41 fixing area for the cylinder/piston unit
42 spring hook
43 undercut
50 spring element, helical compression spring, spring-energy reservoir
58 end face of (82)
59 inner wall of (82)
60 piston-actuating ram
62 guide pin
73 ram plate
75 collar surface, conical
76 piston slide
80 trigger unit 81 trigger cap
82 trigger element
83 widened area
84 return flank
85 edge, sharp
90 tamper-evident seal, banderole, safety element
95 tear-off tab
100 cylinder/piston unit
101 cylinder
102 locking ring
103 end face
104 adhesive ring
105 sealing element
106 bore, nozzle
107 recess in the end face
108 cylinder floor
110 cylinder interior
111 piston
112 annular groove
113 end face, rear; cone
114 sealing ring, seal, sealing element
115 piston recess, bore
118 recess floor of (115)
119 collar on (101)
120 closure cap, adhesive seal
125 pot area
126 windows, on both sides
127 adapter opening
128 stopper
129 foot
131 double cone adapter, bored stopper
132 through-bore
133 recess, internal cone, receiving hollow
134 external cone
140 pump rod
141 tapered thread, V-thread
145 end face, frustoconical
150 needle syringe
151 glass cylinder, container
152 needle
153 piston, needle syringe piston
154 piston rod
155 actuating ram
156 head
157 container interior

What is claimed is:

1. A method for the sterile filling of a needleless disposable injector (4) with a defined dose of an injection solution (1) from a needle syringe (150) including a glass cylinder (151) having a fused-in needle (152), the glass cylinder (151) having a head (156) oriented in the direction of the fused-in needle (152), the disposable injector (4) comprises a cylinder/piston unit (100) with a cylinder (101) and with a single piston (111), the cylinder (101) having a cylinder interior (110), the cylinder (101) having a cylinder floor having a nozzle-like bore (106) ending in a recess (107), a closure cap (120) is removably affixed to a lower portion of the cylinder/piston unit (100), the closure cap (120) having a plate-like foot (129), the plate-like foot (129) having an integral adapter opening (127), said method comprising the steps of:

the defined dose of the injection solution (1) is initially stored in the interior (157) of a container (151) of the needle syringe (150) and the fused-in needle (152) is inserted and held in a bored stopper (131) having a bore (132) therethrough as least as long as the fused-in needle (152) prior to the fused-in needle (152) insertion, the bore (132) having a cross-section corresponding to a cross-section of the fused-in needle (152), the bored stopper (131) includes a receiving hollow (133) for receiving and holding the head (156) of the glass cylinder (151) in a gas-tight and liquid-tight and sterile manner, the bored stopper (131) prior to the sterile filling of the needleless injector (4) closes in a sterile manner the integral adapter opening (127) and simultaneously closes the recess (107) of the cylinder (101) in a sterile, gas-tight and liquid-tight manner, the cylinder interior (110) for the sterile filling is connected to the container interior (157) in a gas-tight and liquid-tight manner through the bored stopper (131) via the fused-in needle (152), and the cylinder/piston unit (100) is filled by pulling back the piston (111) or by pressing a needle syringe piston (153) moveable within the interior (157) of the container (151).

2. A device for the sterile filling of a needleless disposable injector (4) with a defined dose of an injection solution (1) from a needle syringe (150) including a glass cylinder (151) having a fused-in needle (152), the disposable injector (4) comprising a cylinder/piston unit (100) with a cylinder (101) and with a single movable piston (111), the cylinder (101) having a cylinder interior (110), said device comprising:

the defined dose of the injection solution (1) is stored in an interior (157) of a container (151) of the needle syringe (150), the fused-in needle (152) held in a bored stopper (131) having a bore (132) therethrough as least as long as the fused-in needle (152) prior to the fused-in needle (152) insertion, the bore (132) having a cross-section corresponding to a cross-section of the fused-in needle (152), the bored stopper (131) comprises a receiving hollow (133), the glass cylinder (151) having a head (156) oriented in the direction of the fused-in needle (152), and the cylinder interior (110) is operably connectable during the sterile filling of the needleless disposable injector (4) to the container interior (157) via the fused-in needle (152), the head (156) of the glass cylinder (151) for the sterile filling of the needless disposable injector (4) is in insertable relationship within the receiving hollow (133) of the bored stopper (131) in a gas-tight and liquid-tight and sterile manner.

3. The device as claimed in claim 2, wherein a removable pump rod (140) is secured on the piston (111).

4. The device as claimed in claim 2, wherein the bored stopper (131) is made from a synthetic thermoplastic.

5. The device as claimed in claim 2, wherein the needle syringe (150) comprises a movable piston (153) moveable within the interior (157) of the container (151).

6. The device as claimed in claim 5, wherein the needle syringe (150) further comprises a piston rod (154) operably connected to the moveable piston (153).

7. The device as claimed in claim 2, wherein the head (156) has a spherical cap shape.

8. The device as claimed in claim 7, wherein the hollow (133) of the bored stopper (131) has a concave shape for receiving the head (156).

9. The method of claim 1 further comprising the steps of:
after the sterile filling of the needleless disposable injector (4) with a defined dose of an injection solution (1) removing the bored stopper (131) and replacing it with a sterile closure stopper (128) for closing off of the recess (107) in a sterile, gas-tight and liquid-tight manner for interim storage of the needless disposable injector (4).

10. The device as clamed in claim 2, further comprising a sterile closure stopper (128) for interim storage of the needless disposable injector (4) after sterile filling thereof.

\* \* \* \* \*